United States Patent
Hunt et al.

(10) Patent No.: US 9,611,443 B2
(45) Date of Patent: Apr. 4, 2017

(54) NATURAL OIL DERIVATIVES INCLUDING PRIMARY AMINE FUNCTIONAL GROUPS

(71) Applicant: Elevance Renewable Sciences, Inc., Woodridge, IL (US)

(72) Inventors: Zachary Hunt, Simpsonville, SC (US); S. Alexander Christensen, Northwoods, IL (US)

(73) Assignee: Elevance Renewable Sciences, Inc., Woodridge, IL (US)

( * ) Notice: Subject to any disclaimer, the term of this patent is extended or adjusted under 35 U.S.C. 154(b) by 0 days.

(21) Appl. No.: 14/992,360

(22) Filed: Jan. 11, 2016

(65) Prior Publication Data

US 2016/0200859 A1  Jul. 14, 2016

Related U.S. Application Data (63) Continuation of application No. 14/191,862, filed on Feb. 27, 2014, now abandoned.

(60) Provisional application No. 61/779,358, filed on Mar. 13, 2013.

(51) Int. Cl.
| | |
|---|---|
| *C11C 3/00* | (2006.01) |
| *C08G 59/54* | (2006.01) |
| *C08G 59/24* | (2006.01) |
| *C07C 231/02* | (2006.01) |

(52) U.S. Cl.
CPC .............. *C11C 3/00* (2013.01); *C07C 231/02* (2013.01); *C08G 59/245* (2013.01); *C08G 59/54* (2013.01)

(58) Field of Classification Search
CPC ........................................................ C11C 3/00

USPC ........................................................... 554/37
See application file for complete search history.

(56) References Cited

FOREIGN PATENT DOCUMENTS

WO    WO 2011106548 A1 *  9/2011 ........... A61K 31/785

* cited by examiner

*Primary Examiner* — Deborah D Carr
(74) *Attorney, Agent, or Firm* — Kilpatrick Townsend & Stockton LLP (57) ABSTRACT

A compound has Structure I:

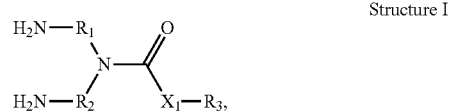

where $R_1$ and $R_2$ independently are $C_2$-$C_{12}$ alkyl groups, $X_1$ is a $C_4$-$C_{28}$ alkyl or alkenyl group, and $R_3$ is H or is a bis(aminoalkyl)amide group having Structure II:

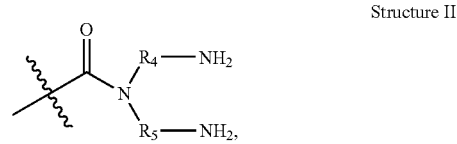

where $R_4$ and $R_5$ independently are $C_2$-$C_{12}$ alkyl groups. The compound may be a reaction product of a metathesized natural oil and a bis(aminoalkyl)amine.

9 Claims, 3 Drawing Sheets

NATURAL OIL DERIVATIVES INCLUDING PRIMARY AMINE FUNCTIONAL GROUPS

REFERENCE TO RELATED APPLICATIONS

This application claims the benefit of U.S. Provisional Application No. 61/779,358 entitled "Natural Oil Derivatives Including Primary Amine Functional Groups" filed Mar. 13, 2013, which is incorporated by reference in its entirety.

BACKGROUND

Compounds having multiple primary amine functional groups are used in a wide variety of applications. Polymeric materials such as polyamides, epoxy polymers, polyureas and other polymers can be formed by condensation reactions of amine-functionalized monomers such as diamines, triamines or tetramines with monomers having other functional groups. Polyamides typically are formed by reaction of a diamine monomer such as ethylenediamine or hexamethylenediamine, with a diacid monomer such as adipic acid or with a diacid chloride monomer such as sebacoyl chloride or terephthaloyl chloride. Epoxy polymers typically are formed by reaction of amine-functionalized monomers such as ethylenediamine, triethylenetriamine, diethylenetriamine, hexamethylenetetramine, tetraethylenepentamine, or amine-terminated polymers or prepolymers with monomers having two or more epoxy groups, such as diglycidyl ethers of bisphenol A or bisphenol F, tetraglycidyl diamine-diphenyl-methane, or multi-glycidyl ethers of phenol formaldehyde novolac polymers. Polyureas typically are formed by reaction of a diamine or triamine monomer with a diisocyanate monomer.

Compounds having multiple primary amine functional groups also are used to form dendritic molecules. Dendritic molecules may be used as solubility enhancers, as catalyst supports, as immunoassay components, and as precursors for advanced materials. Species of the poly(amido amine) (PAMAM) class of dendrimers typically are formed by alternating reaction of ethylenediamine and methyl acrylate. Examples of PAMAM dendrimers include but are not limited to [NH$_2$(CH$_2$)$_2$NH$_2$]: (G=0);dendri PAMAM(NH$_2$)$_4$ and its associated higher generation molecules.

The physical and chemical properties of polymers and of dendritic molecules are affected by the chemical structures of the building blocks used to prepare the polymers and/or dendritic molecules. Alteration of the chemical structure, size and/or concentration of these building blocks can allow for modification of the properties of the polymer or dendritic molecule.

It is desirable to expand the chemical structures present in compounds having multiple primary amine functional groups, so as to expand the useful properties that can be provided by polymers or dendritic molecules formed from the compounds. With regard to polymers, for example, properties such as flexibility, toughness, etc. can be increased by incorporating chemical groups that lower the modulus or that can absorb energy, respectively. This expansion of chemical structures may be accomplished through post-polymerization processing, such as reaction with other reagents or blending with other polymers. It is especially desirable, however, to expand the chemical structures by introducing new chemical structures in the monomeric building blocks from which the polymer is formed. With regard to dendritic molecules, properties such as solubility, chemical reactivity, density, etc. can be changed by incorporating branches having different chain lengths and substitution points.

One potential approach to altering the chemical structure of compounds having multiple primary amine functional groups is to form the compounds from renewable feedstocks. Renewable feedstocks, such as fatty acids or fatty esters derived from natural oils, have opened new possibilities for the development of a variety of industrially useful substances, including specialty chemicals and intermediates. For example, renewable feedstocks can be used to prepare compounds having combinations of properties that were not available with conventional petroleum feedstocks. In another example, renewable feedstocks can be used to prepare compounds more efficiently, without requiring undesirable reagents or solvents, and/or with decreased amounts of waste or side products.

It would be desirable to provide compounds having multiple primary amine functional groups that include previously unavailable chemical structures. Preferably such compounds can be used as substitutes for conventional amine-functionalized compounds, while providing an increase in the renewable content of the final product formed using the compounds. Preferably such compounds can provide useful combinations of properties that are difficult to obtain using compounds formed from conventional petroleum feedstocks.

SUMMARY

The scope of the present invention is defined solely by the appended claims, and is not affected to any degree by the statements within this summary.

In one aspect, a compound is provided that has Structure I:

Structure I where R$_1$ and R$_2$ independently are C$_2$-C$_{12}$ alkyl groups, X$_1$ is a C$_4$-C$_{28}$ alkyl or alkenyl group, and R$_3$ is H or is a bis(aminoalkyl)amide group having Structure II:

Structure II where R$_4$ and R$_5$ independently are C$_2$-C$_{12}$ alkyl groups.

In another aspect, an (aminoalkyl)amide composition is provided that includes the reaction product of a metathesized natural oil and a bis(aminoalkyl)amine.

In another aspect, a method of making an (aminoalkyl) amide composition is provided that includes forming a reaction mixture including a metathesized natural oil and a bis(aminoalkyl)amine, and forming a product mixture including an (aminoalkyl)amide formed from the metathesized natural oil and the bis(aminoalkyl)amine.

BRIEF DESCRIPTION OF THE DRAWINGS

The invention can be better understood with reference to the following drawings and description. The components in the figures are not necessarily to scale and are not intended to accurately represent molecules or their interactions, emphasis instead being placed upon illustrating the principles of the invention. Moreover, in the figures, like referenced numerals designate corresponding parts throughout the different views.

DETAILED DESCRIPTION

To provide a clear and more consistent understanding of the specification and claims of this application, the following definitions are provided.

The terms "reaction" and "chemical reaction" refer to the conversion of a substance into a product, irrespective of reagents or mechanisms involved.

The term "reaction product" refers to a substance produced from a chemical reaction of one or more reactant substances.

The term "alkyl group" refers to a group formed by removing a hydrogen from a carbon of an alkane, where an alkane is an acyclic or cyclic compound consisting entirely of hydrogen atoms and saturated carbon atoms.

The term "alkenyl group" refers to a group formed by removing a hydrogen from a carbon of an alkene, where an alkene is an acyclic or cyclic compound consisting entirely of hydrogen atoms and carbon atoms, and including at least one carbon-carbon double bond. A compound containing an alkenyl group is conventionally referred to as an "unsaturated compound".

The term "functional group" refers to a group that includes one or a plurality of atoms other than hydrogen and $sp^3$ carbon atoms. Examples of functional groups include but are not limited to hydroxyl (—OH), protected hydroxyl, ether (—C—O—C—), ketone (>C=O), ester (—C(=O)O—C—), carboxylic acid (—C(=O)OH), cyano (—C≡N), amido (—C(=O)NH—C—), isocyanate (—N=C=O), urethane (—O—C(=O)—NH—), urea (—NH—C(=O)—NH—), protected amino, thiol (—SH), sulfone, sulfoxide, phosphine, phosphite, phosphate, halide (—X), and the like.

The terms "amine", "amine group" and "amino group" refer to a group formed by removing a hydrogen from ammonia ($NH_3$), from the nitrogen of a primary amine compound ($RNH_2$) or from the nitrogen of a secondary amine compound (R'R"NH), where R, R' and R" are organic groups. A primary amino group may be represented by the structural formula —$NH_2$, and a secondary amino group may be represented by the structural formula —NRH.

The terms "amide", "amide group" and "amido group" refer to a group formed by removing a hydrogen from a carbon atom and/or removing one or both hydrogens from the nitrogen of an organic amide (R—C(=O)—$NH_2$) compound, where R is an organic group. A primary amide group may be represented by the structural formula —C(=O)—$NH_2$, a secondary amide group may be represented by the structural formula —C(=O)—NH—R', and a tertiary amide group may be represented by the structural formula —C(=O)—NR'R", where R' and R" are organic groups.

The term "(aminoalkyl)amide" refers to a compound that includes a least one alkyl and/or alkenyl group, at least one amide group, and at least one aminoalkyl group bonded to the amide nitrogen through a C—N bond.

The term "metathesis catalyst" refers to any catalyst or catalyst system configured to catalyze a metathesis reaction.

The terms "metathesize" and "metathesizing" refer to a chemical reaction involving a single type of olefin or a plurality of different types of olefin, which is conducted in the presence of a metathesis catalyst, and which results in the formation of at least one new olefin product. The phrase "metathesis reaction" encompasses cross-metathesis (a.k.a. co-metathesis), self-metathesis, ring-opening metathesis (ROM), ring-opening metathesis polymerizations (ROMP), ring-closing metathesis (RCM), and acyclic diene metathesis (ADMET), and the like, and combinations thereof.

The terms "natural oils," "natural feedstocks," or "natural oil feedstocks" mean oils derived from plants or animal sources. The term "natural oil" includes natural oil derivatives, unless otherwise indicated. Examples of natural oils include but are not limited to vegetable oils, algal oils, animal fats, tall oils, derivatives of these oils, combinations of any of these oils, and the like. Examples of vegetable oils include but are not limited to canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, camelina oil, pennycress oil, castor oil, and the like, and combinations thereof. Examples of animal fats include but are not limited to lard, tallow, poultry fat, yellow grease, fish oil, and the like, and combinations thereof. Tall oils are by-products of wood pulp manufacture. A natural oil may be refined, bleached, and/or deodorized.

The term "natural oil derivatives" refers to compounds or mixtures of compounds derived from one or more natural oils using any one or combination of methods known in the art. Such methods include but are not limited to saponification, transesterification, esterification, hydrogenation (partial or full), isomerization, oxidation, reduction, and the like, and combinations thereof. Examples of natural oil derivatives include but are not limited to gums, phospholipids, soapstock, acidulated soapstock, distillate or distillate sludge, fatty acids and fatty acid alkyl esters such as 2-ethylhexyl ester, hydroxy-substituted variations thereof of the natural oil, and the like, and combinations thereof. For example, the natural oil derivative may be a fatty acid methyl ester (FAME) derived from the glyceride of the natural oil.

The term "metathesized natural oil" refers to the metathesis reaction product of a natural oil in the presence of a metathesis catalyst, where the metathesis product includes a new olefinic compound. A metathesized natural oil may include a reaction product of two triglycerides in a natural feedstock (self-metathesis) in the presence of a metathesis catalyst, where each triglyceride has an unsaturated carbon-carbon double bond, and where the reaction product includes a "natural oil oligomer" having a new mixture of olefins and esters that may include one or more of metathesis monomers, metathesis dimers, metathesis trimers, metathesis tetramers, metathesis pentamers, and higher order metathesis oligomers (e.g., metathesis hexamers). A metathesized natural oil may include a reaction product of a natural oil that includes more than one source of natural oil (e.g., a mixture of soybean oil and palm oil). A metathesized natural oil may include a reaction product of a natural oil that includes a mixture of natural oils and natural oil derivatives. A metathesized natural oil may include a cross-metathesis reaction product of a natural oil with another substance having a carbon-carbon double bond, such as an olefin or ethylene.

Compounds having a plurality of primary amine functional groups may be formed from a renewable feedstock, such as a renewable feedstock formed through metathesis reactions of natural oils and/or their fatty acid or fatty ester derivatives. When compounds containing a carbon-carbon double bond undergo metathesis reactions in the presence of a metathesis catalyst, some or all of the original carbon-carbon double bonds are broken, and new carbon-carbon double bonds are formed. The products of such metathesis reactions include carbon-carbon double bonds in different locations, which can provide unsaturated organic compounds having useful chemical structures. Renewable feedstocks for compounds having a plurality of primary amine functional groups may include unsaturated compounds having an internal carbon-carbon double bond.

Compounds having a plurality of primary amine functional groups may be used as monomers in polymerization reactions. The use of a monomer containing a metathesized natural oil derivative can provide additional options for providing polymeric materials having useful combinations of properties, including but not limited to mechanical properties, crosslink density, and post-polymerization reactivity. The compounds having a plurality of primary amine functional groups also may be used as intermediates for preparing larger compounds through the reaction of one or more of the plurality of primary amine functional groups with another substance. The use of a monomer and/or an intermediate containing a metathesized natural oil derivative may provide certain advantages over commercial monomers and intermediates, including but not limited to simpler and/or more cost-effective production, reduced variability, improved sourcing, and increased biorenewability.

A compound having a plurality of primary amine functional groups may be an (aminoalkyl)amide represented by Structure I:

Structure I where $R_1$ and $R_2$ independently are $C_2$-$C_{12}$ alkyl groups, $X_1$ is a $C_4$-$C_{28}$ alkyl or alkenyl group, and $R_3$ is selected from the group consisting of H and a N,N-bis(aminoalkyl)amide group represented by Structure II:

Structure II where $R_4$ and $R_5$ independently are $C_2$-$C_{10}$ alkyl groups.

Preferably $R_1$, $R_2$, $R_4$ and $R_5$ independently are $C_2$-$C_{10}$ alkyl groups, $C_2$-$C_8$ alkyl groups, $C_2$-$C_6$ alkyl groups or $C_2$-$C_4$ alkyl groups. In one example, $R_1$, $R_2$, $R_4$ and $R_5$ are the same, and are a $C_2$-$C_{10}$ alkyl group, a $C_2$-$C_8$ alkyl group, a $C_2$-$C_6$ alkyl group, or a $C_2$-$C_4$ alkyl group.

Preferably $X_1$ is a $C_8$-$C_{22}$ alkyl or alkenyl group, or a $C_{10}$-$C_{16}$ alkyl or alkenyl group. $X_1$ may be derived from a natural oil, and preferably is derived from a metathesized natural oil.

In one example, $R_1$ and $R_2$ are $C_2$ alkyl groups, and $R_3$ is H. A compound having a plurality of primary amine functional groups according to this example may be a bis(aminoethyl)amide represented by Structure III:

Structure III where $X_2$ is a $C_4$-$C_{28}$ alkyl or alkenyl group. Preferably $X_2$ is a $C_8$-$C_{22}$ alkyl or alkenyl group, or a $C_{10}$-$C_{16}$ alkyl or alkenyl group. $X_2$ may be derived from a natural oil, and preferably is derived from a metathesized natural oil.

In another example, $R_1$ and $R_2$ are $C_2$ alkyl groups, $R_3$ is the bis(aminoalkyl)amide group represented by Structure (II), and $R_4$ and $R_5$ are $C_2$ alkyl groups. A compound having a plurality of primary amine functional groups according to this example may be a tetra(aminoethyl)diamide represented by Structure IV:

Stuctrue IV where $X_3$ is a $C_4$-$C_{28}$ alkenyl group. Preferably $X_3$ is a $C_8$-$C_{22}$ alkyl or alkenyl group, or a $C_{10}$-$C_{16}$ alkyl or alkenyl group. $X_3$ may be derived from a natural oil, and preferably is derived from a metathesized natural oil.

Preferably the compound having a plurality of primary amine functional groups is derived from a natural oil. More preferably the compound having a plurality of primary amine functional groups is derived from a metathesized natural oil. Preferably the compound having a plurality of primary amine functional groups is the reaction product of a metathesized natural oil and a bis(aminoalkyl)amine. In one example, the reaction product of a metathesized natural oil and a bis(aminoalkyl)amine may be represented by Structure I, III or IV, above.

The metathesized natural oil used to form the compound having a plurality of primary amine functional groups may be the product of a metathesis reaction of a natural oil in the presence of a metathesis catalyst. The metathesis catalyst in this reaction may include any catalyst or catalyst system that catalyzes a metathesis reaction. Any known metathesis catalyst may be used, alone or in combination with one or more additional catalysts. Examples of metathesis catalysts and process conditions are described in paragraphs [0069]-[0155] of US 2011/0160472, incorporated by reference herein in its entirety, except that in the event of any inconsistent disclosure or definition from the present specification, the disclosure or definition herein shall be deemed to prevail. A number of the metathesis catalysts described in US 2011/0160472 are presently available from Materia, Inc. (Pasadena, Calif.).

In some embodiments, the metathesis catalyst includes a transition metal. In some embodiments, the metathesis catalyst includes ruthenium. In some embodiments, the metathesis catalyst includes rhenium. In some embodiments, the metathesis catalyst includes tantalum. In some embodiments, the metathesis catalyst includes nickel. In some embodiments, the metathesis catalyst includes tungsten. In some embodiments, the metathesis catalyst includes molybdenum.

In some embodiments, the metathesis catalyst includes a ruthenium carbene complex and/or an entity derived from such a complex. In some embodiments, the metathesis catalyst includes a material selected from the group consisting of a ruthenium vinylidene complex, a ruthenium alkylidene complex, a ruthenium methylidene complex, a ruthenium benzylidene complex, and combinations thereof, and/or an entity derived from any such complex or combination of such complexes. In some embodiments, the metathesis catalyst includes a ruthenium carbene complex including at least one phosphine ligand and/or an entity derived from such a complex. In some embodiments, the metathesis catalyst includes a ruthenium carbene complex including at least one tricyclohexylphosphine ligand and/or an entity derived from such a complex. In some embodiments, the metathesis catalyst includes a ruthenium carbene complex including at least two tricyclohexylphosphine ligands [e.g., $(PCy_3)_2Cl_2Ru=CH—CH=C(CH_3)_2$, etc.] and/or an entity derived from such a complex. In some embodiments, the metathesis catalyst includes a ruthenium carbene complex including at least one imidazolidine ligand and/or an entity derived from such a complex. In some embodiments, the metathesis catalyst includes a ruthenium carbene complex including an isopropyloxy group attached to a benzene ring and/or an entity derived from such a complex.

In some embodiments, the metathesis catalyst includes a Grubbs-type olefin metathesis catalyst and/or an entity derived therefrom. In some embodiments, the metathesis catalyst includes a first-generation Grubbs-type olefin metathesis catalyst and/or an entity derived therefrom. In some embodiments, the metathesis catalyst includes a second-generation Grubbs-type olefin metathesis catalyst and/or an entity derived therefrom. In some embodiments, the metathesis catalyst includes a first-generation Hoveda-Grubbs-type olefin metathesis catalyst and/or an entity derived therefrom. In some embodiments, the metathesis catalyst includes a second-generation Hoveda-Grubbs-type olefin metathesis catalyst and/or an entity derived therefrom. In some embodiments, the metathesis catalyst includes one or a plurality of the ruthenium carbene metathesis catalysts sold by Materia, Inc. of Pasadena, Calif. and/or one or more entities derived from such catalysts. Representative metathesis catalysts from Materia, Inc. for use in accordance with the present teachings include but are not limited to those sold under the following product numbers as well as combinations thereof: product no. C823 (CAS no. 172222-30-9), product no. C848 (CAS no. 246047-72-3), product no. C601 (CAS no. 203714-71-0), product no. C627 (CAS no. 301224-40-8), product no. C571 (CAS no. 927429-61-6), product no. C598 (CAS no. 802912-44-3), product no. C793 (CAS no. 927429-60-5), product no. C801 (CAS no. 194659-03-9), product no. C827 (CAS no. 253688-91-4), product no. C884 (CAS no. 900169-53-1), product no. C833 (CAS no. 1020085-61-3), product no. C859 (CAS no. 832146-68-6), product no. C711 (CAS no. 635679-24-2), product no. C933 (CAS no. 373640-75-6).

In some embodiments, the metathesis catalyst includes a molybdenum and/or tungsten carbene complex and/or an entity derived from such a complex. In some embodiments, the metathesis catalyst includes a Schrock-type olefin metathesis catalyst and/or an entity derived therefrom. In some embodiments, the metathesis catalyst includes a high-oxidation-state alkylidene complex of molybdenum and/or an entity derived therefrom. In some embodiments, the metathesis catalyst includes a high-oxidation-state alkylidene complex of tungsten and/or an entity derived therefrom. In some embodiments, the metathesis catalyst includes molybdenum (VI). In some embodiments, the metathesis catalyst includes tungsten (VI). In some embodiments, the metathesis catalyst includes a molybdenum- and/or a tungsten-containing alkylidene complex of a type described in one or more of (a) *Angew. Chem. Int. Ed. Engl.*, 2003, 42, 4592-4633; (b) *Chem. Rev.*, 2002, 102, 145-179; and/or (c) *Chem. Rev.*, 2009, 109, 3211-3226, each of which is incorporated by reference herein in its entirety, except that in the event of any inconsistent disclosure or definition from the present specification, the disclosure or definition herein shall be deemed to prevail.

Figure 1:
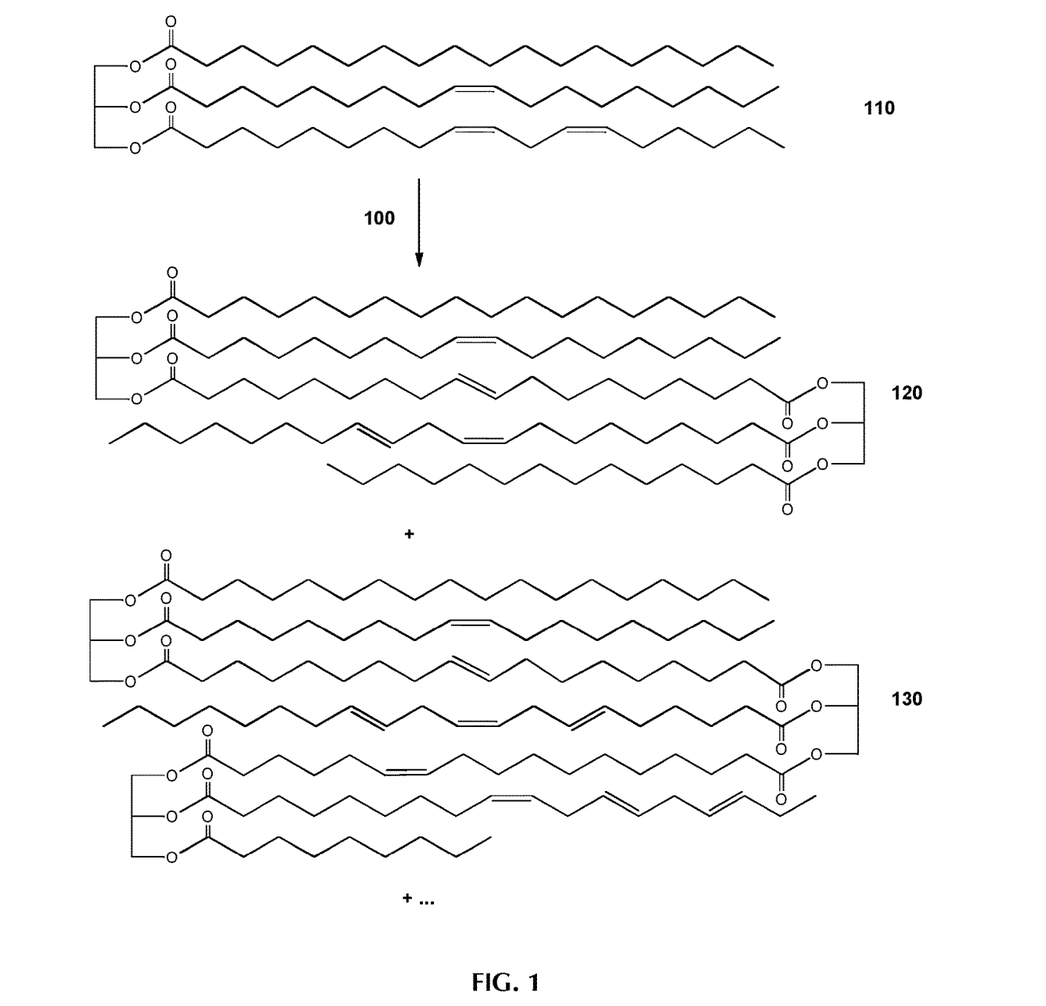
FIG. 1 depicts a reaction scheme for a metathesis reaction of a natural oil.

Metathesis is a catalytic reaction that involves the interchange of alkylidene units among compounds containing one or more double bonds (i.e., olefinic compounds) via the formation and cleavage of the carbon-carbon double bonds. The metathesis reaction of a natural oil containing unsaturated polyol esters can produce oligomers of the unsaturated polyol esters. The resulting oligomers typically contain a mixture of olefins and esters that may include one or more of metathesis monomers, metathesis dimers, metathesis trimers, metathesis tetramers, metathesis pentamers, and higher order metathesis oligomers (e.g., metathesis hexamers, etc.). FIG. 1 depicts chemical structures and reaction schemes related to a metathesis reaction 100 of a natural oil 110, producing metathesis dimer 120, metathesis trimer 130 and higher order metathesis oligomers (not pictured). A metathesis dimer refers to a compound formed when two unsaturated polyol ester molecules are covalently bonded to one another by a metathesis reaction. The molecular weight of the metathesis dimer typically is greater than the molecular weight of the individual unsaturated polyol ester molecules from which the dimer is formed. A metathesis trimer refers to a compound formed when three unsaturated polyol ester molecules are covalently bonded together by metathesis reactions. A metathesis trimer may be formed by the cross-metathesis of a metathesis dimer with an unsaturated polyol ester. A metathesis tetramer refers to a compound formed when four unsaturated polyol ester molecules are covalently bonded together by metathesis reactions. A metathesis tetramer may be formed by the cross-metathesis of a metathesis trimer with an unsaturated polyol ester. Metathesis tetramers may also be formed, for example, by the cross-metathesis of two metathesis dimers. Higher order metathesis oligomers (such as metathesis pentamers, metathesis hexamers, and the like) also may be formed.

The metathesized natural oil may be derived from natural oils such as vegetable oil, algal oil, animal fat, tall oil, derivatives of these oils, or mixtures thereof. Examples of vegetable oils include but are not limited to canola oil, rapeseed oil, coconut oil, corn oil, cottonseed oil, olive oil, palm oil, peanut oil, safflower oil, sesame oil, soybean oil, sunflower oil, linseed oil, palm kernel oil, tung oil, jatropha oil, mustard oil, camelina oil, pennycress oil, castor oil, and the like, and combinations thereof. Examples of animal fats include but are not limited to lard, tallow, poultry fat, yellow grease, fish oil, and the like, and combinations thereof. Examples of natural oil derivatives include but are not limited to metathesis oligomers, gums, phospholipids, soapstock, acidulated soapstock, distillate or distillate sludge, fatty acids and fatty acid alkyl ester such as 2-ethylhexyl ester, hydroxyl-substituted variations of the natural oil, and the like, and combinations thereof. For example, the natural oil derivative may be a fatty acid methyl ester (FAME) derived from the glyceride of the natural oil.

The natural oil may include canola or soybean oil, such as refined, bleached and deodorized soybean oil (i.e., RBD soybean oil). Soybean oil typically includes about 95 percent by weight (wt %) or greater (e.g., 99 wt % or greater) triglycerides of fatty acids. Major fatty acids in the polyol esters of soybean oil include but are not limited to saturated fatty acids such as palmitic acid (hexadecanoic acid) and stearic acid (octadecanoic acid), and unsaturated fatty acids such as oleic acid (9-octadecenoic acid), linoleic acid (9,12-octadecadienoic acid), and linolenic acid (9,12,15-octadecatrienoic acid).

The metathesized natural oil may be a metathesized vegetable oil, a metathesized algal oil, a metathesized animal fat, a metathesized tall oil, a metathesized derivatives of these oils, or a mixture thereof. For example, a metathesized vegetable oil may include metathesized canola oil, metathesized rapeseed oil, metathesized coconut oil, metathesized corn oil, metathesized cottonseed oil, metathesized olive oil, metathesized palm oil, metathesized peanut oil, metathesized safflower oil, metathesized sesame oil, metathesized soybean oil, metathesized sunflower oil, metathesized linseed oil, metathesized palm kernel oil, metathesized tung oil, metathesized jatropha oil, metathesized mustard oil, metathesized camelina oil, metathesized pennycress oil, metathesized castor oil, metathesized derivatives of these oils, or mixtures thereof. In another example, the metathesized natural oil may include a metathesized animal fat, such as metathesized lard, metathesized tallow, metathesized poultry fat, metathesized fish oil, metathesized derivatives of these oils, or mixtures thereof.

Figure 2:
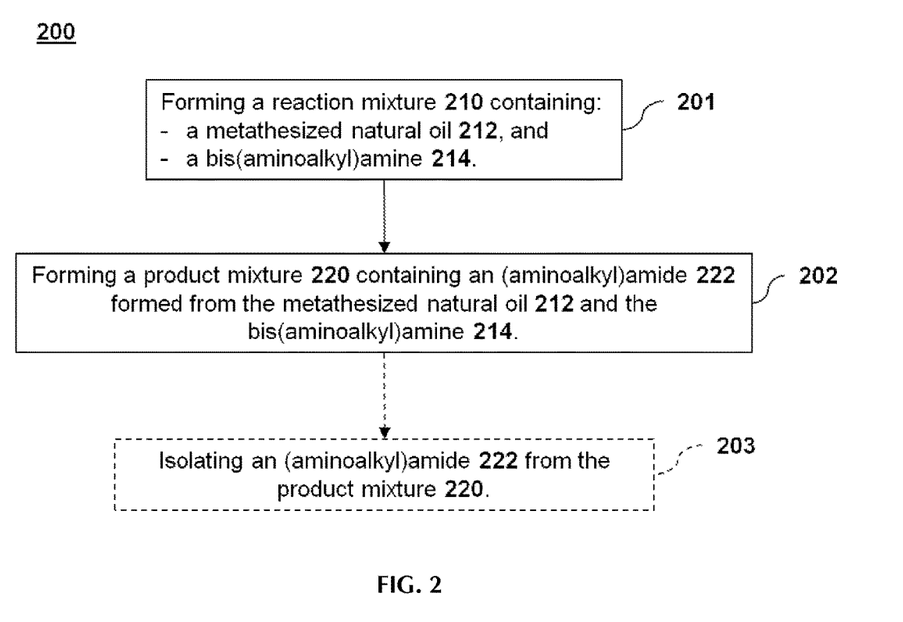
FIG. 2 depicts a method of making an (aminoalkyl)amide.

FIG. 2 depicts a method 200 of making an (aminoalkyl)amide composition. The method 200 includes forming 201 a reaction mixture 210 containing a metathesized natural oil 212 and a bis(aminoalkyl)amine 214; forming 202 a product mixture 220 containing an (aminoalkyl)amide 222 formed from the metathesized natural oil 212 and the bis(aminoalkyl)amine 214; and optionally isolating 203 an (aminoalkyl)amide 222 from the product mixture 220.

The metathesized natural oil 212 may be a metathesized vegetable oil, a metathesized algal oil, a metathesized animal fat, a metathesized tall oil, a metathesized derivatives of these oils, or a mixture thereof, as described above. Preferably the metathesized natural oil 212 includes metathesized soybean oil (MSBO).

The bis(aminoalkyl)amine 214 may be any secondary amine that includes two aminoalkyl groups bonded to the secondary amine nitrogen through C—N bonds. The bis(aminoalkyl)amine 214 may be represented by Structure V:

Structure V where $R_1$ and $R_2$ are as described above regarding Structure I. The two aminoalkyl groups (—$R_1$—$NH_2$ and —$R_2$—$NH_2$) may be the same, or they may be different. The primary amine group may be at any of a number of positions within the aminoalkyl group. Preferably at least one of the aminoalkyl groups is a ω-aminoalkyl group, in which the primary amine group is at the end of the aminoalkyl group opposite that of the C—N bond to the secondary amine nitrogen. Examples of bis(aminoalkyl)amines include bis(2-aminopropyl)amine and N-2-aminopropyl-N-aminoethylamine. Examples of bis(ω-aminoalkyl)amines include but are not limited to diethylenetriamine. Preferably the bis(aminoalkyl)amine 214 includes diethylene triamine.

In some embodiments, the amount of bis(aminoalkyl)amine 214 present in the reaction mixture may be between about 0.1 percent by weight (wt %) and about 30 wt % of the metathesized natural oil in the reaction mixture. The amount of bis(aminoalkyl)amine in the reaction mixture also may be expressed in terms of the ratio of equivalents of secondary amine in the bis(aminoalkyl)amine to ester equivalents in the metathesized natural oil (A:E ratio). For example, in some embodiments, the A:E ratio may be between about 1:100 and about 10:1, or between about 1:10 and about 5:1. In another example, the A:E ratio may be about 1:3, about 2:3, about 1:2, or about 1:1.

The reaction mixture 210 may include one or more other substances, such as a solvent, a base and/or a catalyst, in addition to the metathesized natural oil 212 and the bis(aminoalkyl)amine 214. The metathesized natural oil 212, bis(aminoalkyl)amine 214 and optional other substances may be combined simultaneously or in any order.

In some embodiments, a base may be present in the reaction mixture to increase the rate of reaction between the bis(aminoalkyl)amine and the metathesized natural oil. Examples of bases include but are not limited to sodium carbonate, lithium carbonate, sodium methoxide, potassium hydroxide, sodium hydride, potassium butoxide, potassium carbonate, or mixtures of these. The base may be added to the reaction mixture 210 neat or as a mixture with a solvent such as water, alcohol, or another organic solvent. In some embodiments, the amount of base in the reaction mixture may be between about 0.1 wt % and about 10 wt % of the metathesized natural oil in the reaction mixture, or between about 1 wt % and about 15 wt % of the metathesized natural oil. In some embodiments, the amount of base in the reaction mixture may be between about 1 wt % and about 10 wt % of the metathesized natural oil, between about 0.1 wt % and about 1.0 wt % of the metathesized natural oil, or between about 0.01 wt % and about 0.1 wt % of the metathesized natural oil.

The forming 202 a product mixture 220 containing an (aminoalkyl)amide 222 may include heating the reaction mixture 210. In some embodiments, the rate of reaction between the bis(aminoalkyl)amine 214 and the metathesized natural oil 212 may be increased by heating the reaction mixture, with or without a base, to at least about 100° C., at least about 120° C., at least about 140° C., at least about 160° C., or between about 100° C. and about 200° C. In some embodiments, the reaction may be carried out at an elevated temperature of between about 30 and about 200° C., between about 80 and about 150° C., or between about 100 and about 125° C. In some embodiments, the reaction mixture may be maintained at the elevated temperature for a time sufficient to form an (aminoalkyl)amide 222, such as between about 1 and about 24 hours, or between about 4 and about 24 hours. For example, the reaction mixture may be maintained at the elevated temperature for about 1 hour, about 2 hours, about 4 hours, or about 6 hours. In some embodiments, the reaction may be carried out in an inert atmosphere, such as a nitrogen atmosphere or a noble gas atmosphere. In some embodiments, the reaction may be carried out in an ambient atmosphere.

The optionally isolating 203 an (aminoalkyl)amide 222 from the product mixture 220 may include removing volatile substances under vacuum. For example, the product mixture may be placed under a vacuum for between about 30 minutes and about 1 hour. Volatile substances may include but are not limited to water, solvent, unreacted bis(aminoalkyl)amine, and/or glycerol.

The (aminoalkyl)amide 222 reaction product may have one chemical structure, or the reaction product may be a mixture of compounds having different chemical structures. For example, the (aminoalkyl)amide 222 reaction product may include a mixture of compounds represented by Structure I. For a reaction product that includes a mixture of compounds having different chemical structures, individual compounds may be isolated from the reaction product, or the reaction product may be used as a mixture.

Figure 3:
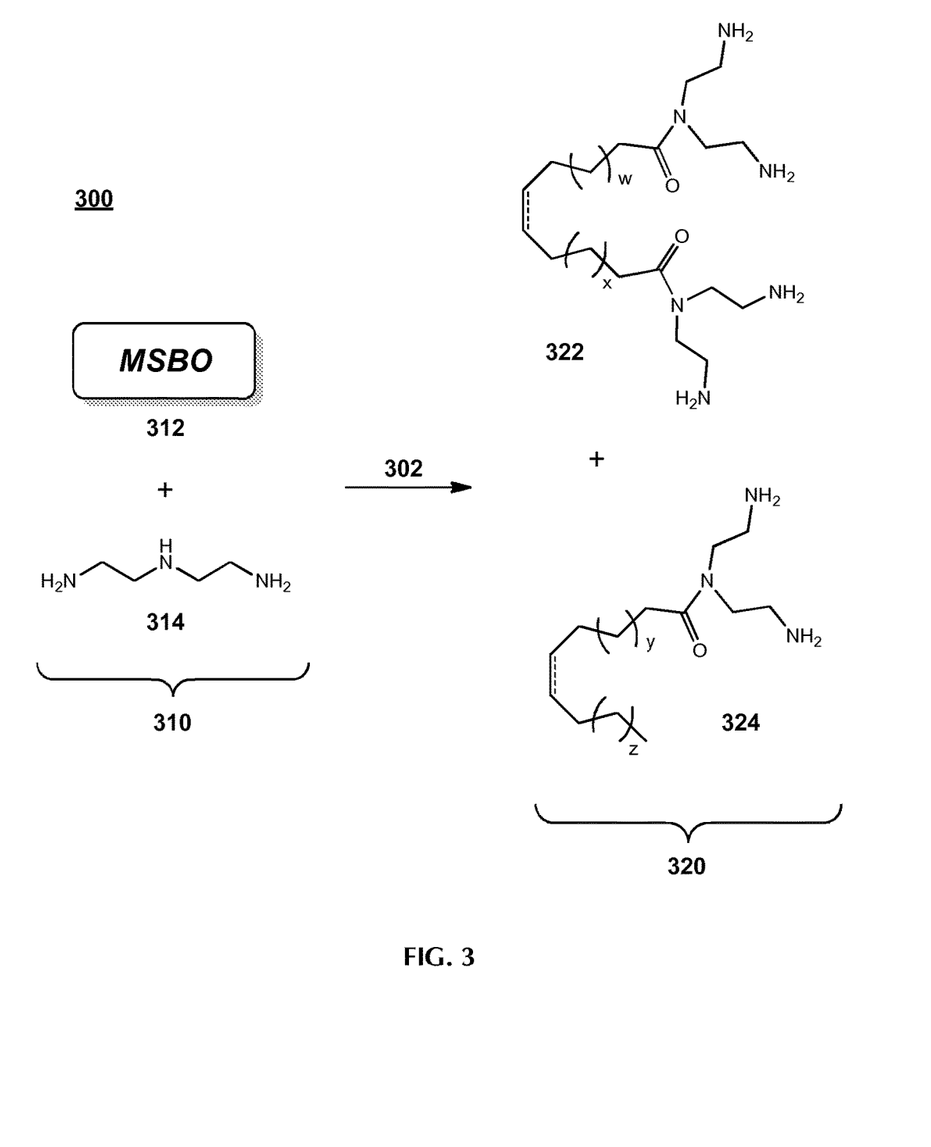
FIG. 3 depicts a representative reaction scheme for a method of forming an (aminoalkyl)amide.

FIG. 3 depicts chemical structures and a reaction scheme for an example of a method 300 of making an (aminoalkyl)amide composition. The method 300 includes forming a reaction mixture 310 containing metathesized soybean oil (MSBO) 312 as the metathesized natural oil and diethylenetriamine 314 as the bis(aminoalkyl)amine. The reaction mixture 310 also may include one or more other substances, such as a solvent, a base and/or a catalyst.

Method 300 further includes forming 302 a product mixture 320 containing (aminoethyl)amide species, such as 322 and/or 324. In species 322 and 324, w, x, y and z independently are integers from 0 to 18, such that the total number of carbon atoms between the amido groups is from 6 to 28, and the partially dashed double line indicates that species may or may not include one or more carbon-carbon double bonds. The forming 302 may include heating the reaction mixture as described above, including maintaining the reaction mixture at a temperature of from about 30° C. to about 200° C. for a time sufficient to form (aminoalkyl)amide species. The tetra(aminoethyl)diamide species 322 and bis(aminoethyl)amide species 324 are exemplary, as the product mixture 320 may include a number of different species of (aminoethyl)amides consistent with Structure I. Structural variables between the species include but are not limited to the presence and number of carbon-carbon double bonds, the number of carbon atoms in the organic group bonded to the (aminoethyl)amide group(s), and branching.

Method 300 further may include isolating an (aminoethyl)amide species. As noted above, isolating one or both of the (aminoethyl)amide species may include removing volatile substances under vacuum, where the volatile substances may include but are not limited to water, solvent, unreacted diethylenetriamine 314, and/or glycerol. The optional isolating may provide a mixture of (aminoalkyl)amide species, or it may provide a single (aminoalkyl)amide species.

A compound having a plurality of primary amine functional groups, such as the reaction product of a metathesized natural oil and a bis(aminoalkyl) amine and/or a compound represented by Structure I above, may be used in a polymerization reaction. A monofunctional monomer, such as a monomer having Structure I in which —R$_3$ is H, may be used as a chain extender in a polymer. A difunctional monomer, such as a monomer having Structure I in which —R$_3$ is a bis(aminoalkyl) amide group, may be used as a crosslinker in a polymer. A mixture of monofunctional and difunctional monomers may be used to provide both chain extension and crosslinking features to a polymer.

In one example, the compound having a plurality of primary amine functional groups may be reacted with monomers having two or more epoxy groups to form an epoxy polymer. Examples of monomers having two or more epoxy groups include but are not limited to diglycidyl ethers of bisphenol A or bisphenol F, tetraglycidyl diamine-diphenylmethane, and multi-glycidyl ethers of phenol formaldehyde novolac polymers. The compound having a plurality of primary amine functional groups may account for all of the amine-functionalized monomer in the polymerization reaction, or one or more other amine-functionalized monomers, such as such as ethylene diamine, triethylenetriamine, diethylenetriamine, hexamethylenetetramine, tetraethylenepentamine or amine-terminated polymers or prepolymers, may be present in the polymerization.

In another example, the compound having a plurality of primary amine functional groups may be reacted with a diacid monomer or a diacid chloride monomer to form a polyamide. Examples of diacid monomers include but are not limited to adipic acid. Examples of diacid chloride monomers include but are not limited to sebacoyl chloride and terephthaloyl chloride. The compound having a plurality of primary amine functional groups may account for all of the amine-functionalized monomer in the polymerization reaction, or one or more other amine-functionalized monomers, such as such as ethylenediamine or hexamethylenediamine, may be present in the polymerization.

A compound having a plurality of primary amine functional groups, such as the reaction product of a metathesized natural oil and a bis(aminoalkyl) amine and/or a compound represented by Structure I above, may be used to form a dendritic molecule. In one example, the compound having a plurality of primary amine functional groups may be used as a substitute for some or all of the ethylenediamine typically used in the synthesis of PAMAM dendrimers. In another example, the compound having a plurality of primary amine functional groups may be used as the core in the divergent synthesis of a dendrimer. Reaction of the compound with methyl acrylate, followed by reaction with ethylenediamine, may provide a dendrimer analogous to the PAMAM system, but with a core that is more flexible and less sterically hindered.

The following examples and representative procedures illustrate features in accordance with the present teachings, and are provided solely by way of illustration. They are not intended to limit the scope of the appended claims or their equivalents, and numerous variations can be made to the following examples that lie within the scope of these claims.

EXAMPLES

Example 1

Formation of (Aminoalkyl)amide Compounds

An (aminoalkyl)amide compound was formed by reacting a metathesized natural oil and a bis(aminoalkyl)amine. Diethylenetriamine (DETA) (106.18 grams (g)) and sodium methoxide (1.11 g) were combined in a flask equipped with a condenser, and the mixture was heated to 115° C. and stirred. To this mixture, metathesized soybean oil (MSBO; 250 g) was added dropwise.

Table 1 lists the reactants present in the reaction mixture. The saponification value (SAP) of MSBO was determined using the standard AOCS (American Oil Chemists' Society)

procedure. The average molecular weight between ester groups in the MSBO was approximately 56,100/SAP=56,100/210=267.2 Daltons.

TABLE 1

Reactants used to form (aminoalkyl)amide compounds

| | MSBO | Diethylenetriamine | Sodium methoxide |
|---|---|---|---|
| molecular weight | 210* | 103.17 g/mol | 54.02 g/mol |
| mass | 250 g | 106.18 g | 1.11 g |
| moles | 0.9357 | 1.0292 | 0.0206 |
| equivalents | 1 | 1.1 | 0.022 |

*saponification value

The mixture was maintained at 115° C. for 2 hours after the MSBO addition was complete. The mixture was allowed to cool, and was then dissolved in diethyl ether, washed with a saturated sodium chloride solution, and dried. The ether was removed from the product by rotary evaporation to provide a mixture of monomers having at least two primary amine functional groups and containing a group derived from the MSBO.

Characterization of the product by Fourier Transform Infrared Spectroscopy (FTIR) was consistent with full conversion of the ester groups of the MSBO to N,N-bis(aminoethyl)amide groups. While neither desiring to be bound by any particular theory nor intending to limit in any measure the scope of the appended claims or their equivalents, it is presently believed that the product may be represented by Structures III and/or IV, above.

Example 2

Formation of Epoxy Thermoset

A polymer was formed by reacting bisphenol A diglycidyl ether with a compound having a plurality of primary amine functional groups. The (aminoalkyl)amide compound of Example 1 and bisphenol A diglycidyl ether were combined, resulting in a hard epoxy polymer product.

The foregoing detailed description and accompanying drawings have been provided by way of explanation and illustration, and are not intended to limit the scope of the appended claims. Many variations in the presently preferred embodiments illustrated herein will be apparent to one of ordinary skill in the art, and remain within the scope of the appended claims and their equivalents.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims can, alternatively, be made to depend in the alternative from any preceding claim—whether independent or dependent and that such new combinations are to be understood as forming a part of the present specification.

What is claimed is:

1. A polymer, which comprises constitutional units formed from a reaction mixture comprising: (a) a monomer having two or more epoxy groups; and (b) a compound according to Structure I:

Structure I wherein:
$R_1$ and $R_2$ independently are $C_2$-$C_{12}$ alkyl groups;
$X_1$ is a $C_4$-$C_{28}$ alkyl group or a $C_4$-$C_{28}$ alkenyl group; and
$R_3$ is a hydrogen atom or a bis(aminoalkyl)amide group according to Structure II:

Structure II wherein $R_4$ and $R_5$ independently are $C_2$-$C_{12}$ alkyl groups.

2. The polymer of claim 1, wherein $R_1$, $R_2$, $R_4$, and $R_5$ independently are $C_2$-$C_6$ alkyl groups.

3. The polymer of claim 1, wherein $X_1$ is a $C_{10}$-$C_{16}$ alkyl group or a $C_{10}$-$C_{16}$ alkenyl group.

4. The polymer of claim 3, wherein $R_3$ is a hydrogen atom and $R_1$ and $R_2$ are $C_2$ alkyl groups.

5. The polymer of claim 3, wherein $R_3$ is a bis(aminoalkyl)amide group according to Structure II and $R_1$, $R_2$, $R_4$, and $R_5$ are $C_2$ alkyl groups.

6. The polymer of claim 5, wherein $R_1$, $R_2$, $R_4$, and $R_5$ are —$CH_2$—$CH_2$—.

7. The polymer of claim 1, wherein the monomer having two or more epoxy groups is bisphenol A diglycidyl ether, bisphenol F diglycidyl ether, tetraglycidyl diamine-diphenyl-methane, or a multi-glycidyl ether of phenol formaldehyde novolac polymers.

8. The polymer of claim 7, wherein the monomer having two or more epoxy groups is bisphenol A diglycidyl ether.

9. The polymer of claim 7, wherein the monomer having two or more epoxy groups is bisphenol F diglycidyl ether.

* * * * *